United States Patent [19]

Firestone

[11] 4,388,475
[45] Jun. 14, 1983

[54] ALLYLSULFOXIDE ENZYME INHIBITORS

[75] Inventor: Raymond A. Firestone, Fanwood, N.J.

[73] Assignee: Merck & Co., Inc., Rahway, N.J.

[21] Appl. No.: 147,659

[22] Filed: May 7, 1980

Related U.S. Application Data

[63] Continuation-in-part of Ser. No. 66,603, Aug. 15, 1979, abandoned.

[51] Int. Cl.³ .................... C07C 147/08; A61K 31/10
[52] U.S. Cl. .................................. 564/341; 562/430;
564/440; 424/94; 564/503; 564/509; 424/250;
564/510; 568/24; 424/251; 568/25; 424/263;
424/270; 424/272; 424/273 R; 424/275;
424/303; 424/304; 424/308; 424/309; 260/456
A; 260/465 F; 544/298; 544/316; 544/318;
544/319; 544/408; 546/294; 548/182; 548/186;
548/225; 548/228; 548/229; 548/337; 549/65;
549/66; 560/11; 560/12; 560/17; 562/429
[58] Field of Search ......... 560/17; 260/465 F, 456 A;
562/240; 424/304, 309, 94; 564/341

[56] References Cited

U.S. PATENT DOCUMENTS

| | | | |
|---|---|---|---|
| 2,358,786 | 9/1944 | Bogert et al. | 564/340 |
| 3,221,054 | 11/1965 | Arnold et al. | 560/17 |
| 3,369,025 | 2/1968 | Bolhofer | 424/263 |
| 3,519,686 | 7/1970 | Nair | 560/17 |
| 3,652,646 | 3/1972 | Leigh et al. | 424/268 |
| 3,712,913 | 1/1973 | Chodaekar et al. | 560/17 |
| 3,950,542 | 4/1976 | Kalopissis et al. | 424/316 |
| 4,155,907 | 5/1979 | Dunbar et al. | 424/248.5 |

FOREIGN PATENT DOCUMENTS

| | | |
|---|---|---|
| 2021229 | 11/1970 | Fed. Rep. of Germany . |
| 474494 | 8/1969 | Switzerland ............ 564/340 |
| 1082072 | 9/1967 | United Kingdom . |
| 1357154 | 6/1974 | United Kingdom . |
| 1527219 | 10/1978 | United Kingdom . |

OTHER PUBLICATIONS

Walsh, "Horizons Biochem. Biophys.," vol. 3, 1977, pp. 36-81.
Mislow et al., "J. Amer. Chem. Soc.," vol. 90, 1968, pp. 4869-4876.
Mislow et al., "J. Amer. Chem. Soc.," vol. 92, 1970, pp. 2100-2104.
Evans et al., "J. Amer. Chem. Soc.," vol. 94, 1972, pp. 3672-3674.

Primary Examiner—Donald G. Daus
Assistant Examiner—James H. Turnipseed
Attorney, Agent, or Firm—William H. Nicholson; Mario A. Monaco

[57] ABSTRACT

Organic sulfoxides having a latent allyl group bound to the sulfur are enzyme inhibitors of the suicide or $K_{cat}$ type.

2 Claims, No Drawings

ALLYLSULFOXIDE ENZYME INHIBITORS

BACKGROUND OF THE INVENTION

This is a continuation-in-part of copending application Ser. No. 66,603, filed Aug. 15, 1979 now abandoned.

This invention is concerned with a novel class of enzyme inhibitors of the suicide of $K_{cat}$ type in which the latent reactive group is an allylsulfoxide which is in reversible equilibrium with an allyl sulfenate:

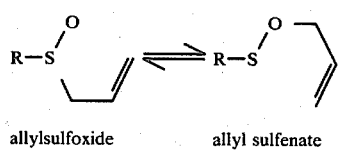

(A)

allylsulfoxide         allyl sulfenate

Suicide enzyme inhibitors are substances bearing a latent reactive group that is unmasked by the target enzyme itself, and which after being unmasked, immediately reacts with the enzyme in an irreversible manner, inactivating it. Enzyme inhibitors of the suicide type are known in the art but until now almost invariably have employed a Michael acceptor as the reactive species and these are described by Walsh in *Horizons Biochem. Biophys.*, 3, 36–81 (1977).

The allysulfoxide-allyl sulfenate equilibrium of reaction scheme A) is also known in the art and has been studied as an interesting chemical reaction by Mislow et al., *J. Amer. Chem. Soc.*, 90, 4869 (1968); 92, 2100 (1970) and Evans et al., *J. Amer. Chem. Soc.*, 94, 3672 (1972). Generally, allylsulfoxides are unreactive, but allyl sulfenates are highly reactive electrophiles, and would be expected to capture almost any nucleophile (Nu) in an enzyme that happens to be near it at the moment it is formed:

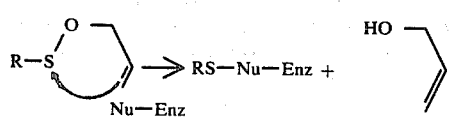

(B)

Usually the nucleophile is one from the protein portion (prosthetic group) of the enzyme, such as a sulfhydryl, amino, hydroxy, imidazolyl or the like. Once the nucleophile is sulfenylated, the enzyme is altered from its native, active form and can no longer function in its intended role as a biochemical catalyst.

In the present invention, the latency of the allylsulfoxide group is generally secured as a sulfoxide carrying a β-leaving group or as a vinylsulfoxide, neither of which is especially reactive. However, in a properly designed inhibitor, the target enzyme recognizes the group Z as a substrate, and removes a proton. Then (in the case of the β-leaving group), the leaving group X departs leaving the allylsulfoxide, or (with the vinylsulfoxide) the proton is re-deposited with allylic rearrangement, creating the allylsulfoxide:

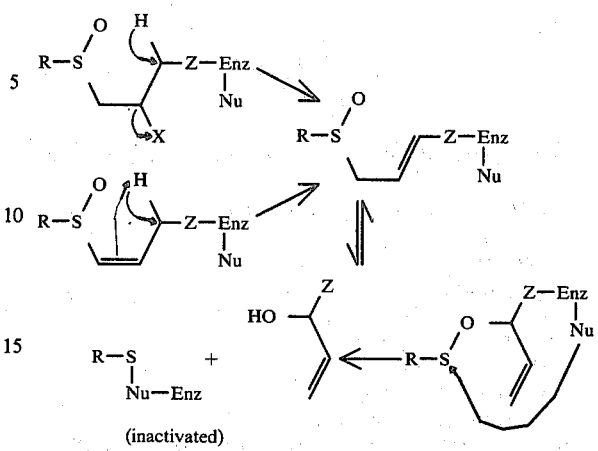

In either case, the allylsulfoxide can now rearrange to the allyl sulfenate which captures the enzyme's nucleophile, inactivating it.

The allylsulfoxide-allyl sulfenate rearrangement is facilitated by the nature of the R group attached to the sulfur: the stronger the electron withdrawing nature of R the better, for example, p-nitrophenyl. Steric acceleration of the rearrangement is also provided by bulky o-substituents such as o-alkyl and o,o'-dialkyl when R is substituted-phenyl. Bulky groups such as alkyl and chloro substituted on the carbon chain adjacent to the sulfur atom also provide steric acceleration. Another type of electronic acceleration of the rearrangement is provided by having an electron withdrawing group, such as cyano, alkoxycarbonyl or the like substituted on the carbon β-to the sulfur atom or, in other words, on the middle carbon of the allyl group.

It is, therefore, an object of this invention to provide a group of novel organic sulfoxides wherein one of the substituents on the sulfur carries such other functional group or groups as to be a latent allyl group which becomes unmasked upon reaction with a target enzyme and which function as enzyme inhibitors of the suicide type.

It is another object of this invention to provide a useful tool of biochemical research in the form of selective, very active enzyme inhibitors.

It is a further object of this invention to provide means for inhibiting enzymes, both *in vitro* and *in vivo* with the novel organic sulfoxides of this invention.

It is a still further object to provide a method of treating disease states, the progress of which is dependent on the activity of enzymes, which comprises the administration of an effective amount of an enzyme inhibitor of this invention.

It is also an object of this invention to provide pharmaceutical formulations comprising one or more of the novel enzyme inhibitors of this invention.

DETAILED DESCRIPTION OF THE INVENTION

This invention comprises, as one embodiment, a new class of $K_{cat}$ suicide enzyme inhibitors which are organic sulfoxides of structural formula:

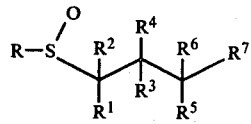

or a pharmaceutically acceptable salt thereof, wherein R is
(a) phenyl, either unsubstituted or substituted with such as
(1) nitro,
(2) cyano,
(3) $C_{1-3}$ alkylsulfonyl,
(4) $C_{1-3}$ alkoxycarbonyl,
(5) o-$C_{1-3}$ alkyl,
(6) o,o-di($C_{1-3}$ alkyl), or
(7) di(trifluoromethyl);
(b) trihalomethyl, such as trifluoromethyl or trichloromethyl;
(c) heteroaryl such as
(1) thiazolyl,
(2) imidazolyl,
(3) pyridinyl,
(4) pyrazinyl,
(5) oxazolyl,
(6) pyrimidinyl, or
(7) thienyl; and $R^1$ is hydrogen or aminomethyl,
$R^2$ and $R^5$ are hydrogen;
$R^3$ is a facile leaving group such as
(a) halo such as fluoro, chloro, bromo, or iodo,
(b) $C_{2-4}$ alkanoyloxy,
(c) toluenesulfonyloxy,
(d) benzenesulfonyloxy,
(e) $C_{1-3}$ alkanesulfonyloxy,
(f) p-nitrobenzoyloxy, and
(g) hydroxy, or
$R^2$ and $R^3$ taken together form a double bond;
$R^4$ is hydrogen, or an electron withdrawing group such as fluoro, chloro, —$C_{1-3}$ alkoxycarbonyl, cyano, trihalomethyl such as trichloromethyl or trifluoromethyl, or the like;
$R^6$ is hydrogen, —COOH, or —$CH_2CH_2COOH$; and
$R^7$ is —OH, —$NH_2$, —SH, —$CH_2OH$, $$-CH\begin{matrix}COOH\\NH_2\end{matrix},$$

or —$OPO_3R^8R^9$, wherein
$R^8$ and $R^9$ are independently hydrogen or $C_{1-3}$ alkyl.

Pharmaceutically acceptable salts are also contemplated to be within the scope of the present invention and are those prepared from inorganic or organic acids known in the art to provide pharmaceutically acceptable salts, such as hydrochloric, sulfuric, hydrobromic, phosphoric, tartaric, fumaric, citric, malic, maleic, ascorbic, acetic, lactic, oleic, pamoic, palmitic, isethionic, pyroglutamic acid, or the like. Also contemplated are the alkali metal salts, such as the sodium and potassium salts of the acidic enzyme inhibitors. These salts and others such as those resulting from synthetic procedures are readily interconvertible from one to another by well-known methods.

The novel enzyme inhibitors of this invention have a high, specific activity and thus are useful tools for the research biochemist and pharmacologist in studies of biochemical changes in vitro, and in vivo, and in biochemical assays for natural enzyme substrates and the like by standard enzymological procedures. The enzyme inhibitors are active, in vitro, at concentrations as low as about 0.1 mM but are generally employed at concentrations of 1 to about 2 mM.

For in vivo studies, the novel enzyme inhibitors of this invention are administered orally or parenterally, preferably the latter and preferably intravenously. Dosages of about 0.1 mg/kg to about 50 mg/kg are used depending on the purpose of the experiment, which may require the use of the threshold dose or the dose to produce total inhibition of a particular enzyme.

Many disease states of mammals, including humans, are known to depend for their progress on the activity or hyperactivity of particular enzymes and treatment of many of these diseases have been devised around inhibitors of these enzymes. Accordingly, the novel enzyme inhibitors of this invention have utility in the study of certain disease states and in their treatment.

Generally the novel enzyme inhibitors of this invention produce the desired effect when administered at from 0.1 to about 500 mg/kg body weight, preferably at from 1 to about 50 mg/kg of body weight. The preferred form of delivery of the instant compounds to domestic animals is by solution in drinking water or by inclusion in preformulated feedstuffs. For human and animal administration, any of the usual pharmaceutical oral forms may be employed such as tablets elixirs, aqueous suspensions or the like comprising from about 0.1 to about 500 mg of the compounds of this invention. Sterile solutions (representatively given for human treatment) for injection comprising from about 0.1 to about 500 mg of the compounds of this invention given two to four times daily are also suitable means of delivery.

Representative specific members of the new class of suicide enzyme inhibitors are shown in Table I along with the enzyme to be inhibited and the pharmacological or medical effect to be elicited. In each case, R' represents o- or p-nitrophenyl, o- or p-cyanophenyl, o- or p-methoxycarbonylphenyl, o- or p-methylsulfonylphenyl, o,p-di(trifluoromethyl)phenyl, trifluoromethyl, trichloromethyl, 2-pyrimidinyl, 2-pyridyl, 2-imidazolyl, 2-thienyl, 2-thiazolyl, 2-oxazolyl, o-methylphenyl, o-ethylphenyl, o-propylphenyl, o,o-di(methyl)phenyl, o,o-di(ethyl)phenyl, or o,o-di(propyl)phenyl.

TABLE I

| INHIBITOR | PREPARATIVE METHOD EXAMPLE | ENZYME INHIBITED | USE, PHARMACOLOGICAL OR MEDICAL EFFECT |
| --- | --- | --- | --- |
| 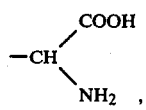 | 1, 2 | monoamine oxidase | antidepressant |

TABLE I-continued

| INHIBITOR | PREPARATIVE METHOD EXAMPLE | ENZYME INHIBITED | USE, PHARMACOLOGICAL OR MEDICAL EFFECT |
|---|---|---|---|
| R—S(O)—CH=CH—CH₂—NH₂ | | | |
| R—S(O)—CH=C(COOCH₃)—CH₂—NH₂ | 3 | | |
| R—S(O)—CH₂—CHCl—CH(NH₂)—COOH | 1, 2 | alanine racemase | antibacterial |
| R—S(O)—CH=C(COOH)—NH₂ | 3 | S—adenosyl methionine decarboxylase | antipsoriasis |
| R—S(O)—CH=C(CH₃)—CH₂—OH | 3 | isopentenyl pyrophosphate isomerase | anti-atherosclerosis |
| R—S(O)—CH₂—CHCl—CH(OH)—COOH | 1, 2 | glycollate oxidase | anti-renal lithiasis |
| R—S(O)—CH=CH—CH(OH)—COOH | 3 | lactate dehydrogenase | antipsoriasis |
| R—S(O)—CH₂—CHCl—CH₂—CH₂—OH | 1, 2 | alcohol dehydrogenase | anti-alcoholism |
| R—S(O)—CH=CH—CH₂—OH | 3 | | |
| R—S(O)—CH=C(CF₃)—CH₂—OH | 3 | | |
| R—S(O)—CH₂—CH(OH)—CH(NH₂)—COOH | 1, 2 | serine transhydroxymethylase | antipsoriasis |
| R—S(O)—CH₂—CHCl—CH₂—CH(NH₂)—COOH | 1 | cystathionine γ-synthetase methionine γ-lyase | antibacterial |
| R—S(O)—CH=CH—CH₂—CH(NH₂)—COOH | 3 | | |
| R—S(O)—CH₂—CHCl—CH(NH₂)—CH₂—COOH | 1 | GABA transaminase | anticonvulsant |
| R—S(O)—CH=CH—CH(NH₂)—CH₂—COOH | 3 | | |

TABLE I-continued

| INHIBITOR | PREPARATIVE METHOD EXAMPLE | ENZYME INHIBITED | USE, PHARMACOLOGICAL OR MEDICAL EFFECT |
|---|---|---|---|
| 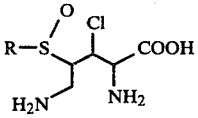 | 1 | ornithine decarboxylase | antipsoriasis antiarthritic anticancer |
| 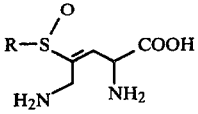 | 3 | | |

The mechanism by which some of the novel compounds demonstrate their enzyme inhibiting properties are depicted schematically below.

In the simpler cases in which the functional group, Z, is an amine the mechanism is as follows:

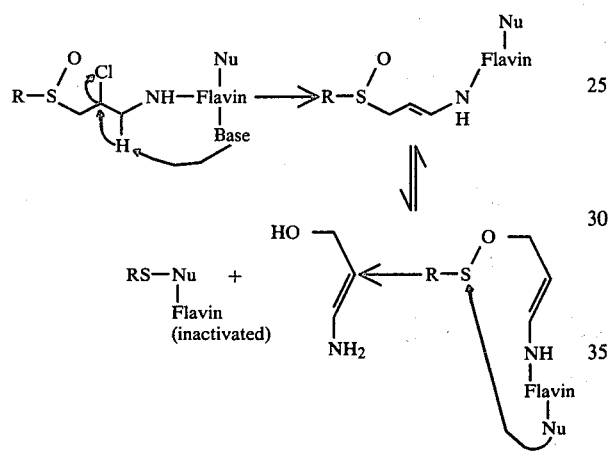

The novel process for preparing the novel compounds of this invention comprises oxidation of an aromatic thio compound of structure:

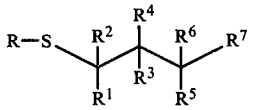

wherein R, and $R^{1-7}$ are as previously defined with the exception that any of the substituents $R^{1-7}$ which are sensitive to the conditions of oxidation of sulfide to sulfoxide carry protective groups.

The oxidizing agent is such as 1-chlorobenzotriazle, $H_2O_2/V_2O_5$, $SO_2Cl_2/H_2O$/silica gel, $Cl_2$, $Br_2$, $NaIO_4$, acetyl nitrate $Tl(NO_3)_3$, or a peracid such as m-chlorperbenzoic acid, preferably the latter. The oxidation with a peracid is conducted at temperatures from $-70°$ C. to about $30°$ C., preferably at about $0°-25°$ C., in an organic solvent such as an aromatic solvent, for example benzene, toluene or the like; or a chlorinated hydrocarbon such as tetrachloroethylene, chloroform, methylene chloride or the like, for times of a few minutes to about 4 hours.

After the oxidation is substantially complete, any protective groups present are removed by standard procedures such as treatment with a strong organic acid such as trifluoroacetic acid to remove t-butyloxycarbonyl groups from amines and to cause deesterification; strong mineral acids to remove trityl groups from amines; and strong bases such as sodium hydroxide or potassium hydroxide to saponify esters.

EXAMPLE 1

2-Amino-4-chloro-5-(p-nitrophenyl)sulfinylpentanoic acid

Step A: Preparation of N-BOC allylglycine

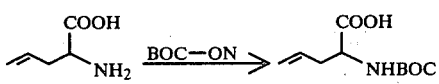

A mixture of 884 mg of allylglycine, 4.6 ml of water, 4.6 ml of dioxane, 1.6 ml of triethylamine and 2.08 g BOC-ON is stirred for 3.75 hrs at $25°$ C. Then 15 ml of water and 20 ml of ether are added. The aqueous layer is separated, washed with ether, acidified to pH 2 with HCl, and filtered to isolate the crystalline product, 1.4. g, m.p. $109°$ C.

Step B: Preparation of N-BOC allylglycine benzhydryl ester

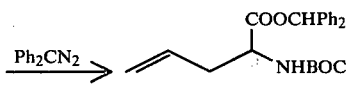

N-BOC allylglycine, 269 mg, is treated with 243 mg of diphenyldiazomethane in 25 ml of acetonitrile for one hour. The solvent is evaporated. Benzene is added, washed with aqueous $NaHCO_3$ and brine, dried with $MgSO_4$, filtered and evaporated, affording crystalline product which is washed with hexane and dried, 380 mg, m.p. $79°$ C.

Step C: Preparation of N-BOC 2-amino-4-chloro-5-(p-nitrophenyl)thiopentanoic acid benzhydryl ester

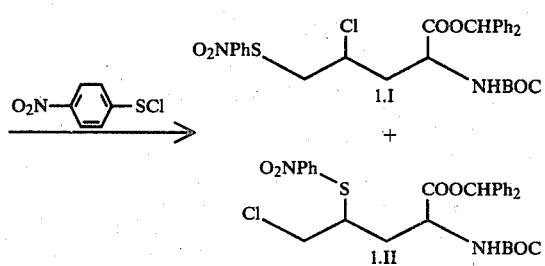

To 255 mg of N-BOC allylglycine benzhydryl ester in 1 ml of CH$_2$Cl$_2$ is added dropwise over 45 minutes at −18° C. under N$_2$, 152 mg of p-nitrophenylsulfenyl chloride in 1 ml of CH$_2$Cl$_2$. After an hour at 25° C. the solvent is evaporated, leaving a mixture of product I and its regioisomer II which is partially separated by preparative thin layer chromatography on silica gel with 50:1 (v/v) CHCl$_3$:EtOAc. The product, admixed with some II is obtained at Rf 0.4.

Step D: Preparation of N-BOC 2-amino-4-chloro-5-(p-nitrophenyl)sulfinylpentanoic acid benzhydryl ester

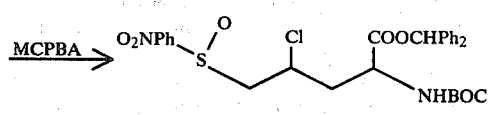

To 128 mg of product from the previous step in 4 ml of CH$_2$Cl$_2$ at 0° C. under N$_2$ with stirring over 1 hour is added 45.5 mg of m-chloroperbenzoic acid (MCPBA) (85% pure) in 4 ml of CH$_2$Cl$_2$. After 0.5 hour at 25° C. the solution is washed with aqueous NaHCO$_3$, dried with MgSO$_4$, filtered and evaporated to afford 131 mg of product admixed with its regioisomer. Complete separation is afforded by preparative thin layer chromatography on silica gel with 4:1 (v/v) CHCl$_3$-EtOAc. The rearmost band, Rf 0.3, provides 40 mg of pure product.

Step E: Preparation of 2-amino-4-chloro-5-(p-nitrophenyl)sulfinyl pentanoic acid

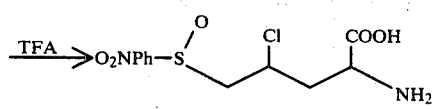

The product from Step D, 39 mg, is dissolved in 0.2 ml of anisole and treated at 0° C. with 1.0 ml trifluoracetic acid (TFA) for 10 minutes. The excess TFA and then the anisole are pumped off in vacuo. To the residue are added a few ml each of water and CH$_2$Cl$_2$. The water layer is separated and evaporated in vacuo, affording 26 mg of pure product as its TFA salt.

EXAMPLE 2

1-Amino-2-chloro-3-(p-nitrophenyl)sulfinylpropane

Step A: Preparation of N-BOC allylamine (2.I)

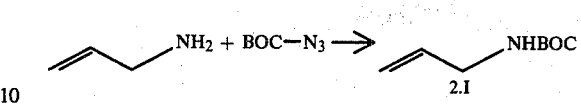

A mixture of 3.00 ml of allylamine, 30 ml of CH$_2$Cl$_2$, 5.85 ml of triethylamine and 5.81 ml of BOC-azide is prepared at 0° C. and stirred at 25° C. for 16.5 hours while protected from moisture. It is then treated with 2 ml of water for 20 minutes, evaporated, treated with ethyl acetate, extracted successively with water, aqueous pH 2 phosphate buffer, water, aqueous K$_2$HPO$_4$ and brine, dried with MgSO$_4$, filtered and evaporated to afford 5.54 g of product, m.p. 37° C.

Step B: Preparation of N-BOC 1-amino-2-chloro-3-(p-nitrophenyl)thiopropane (2.II and 2.III)

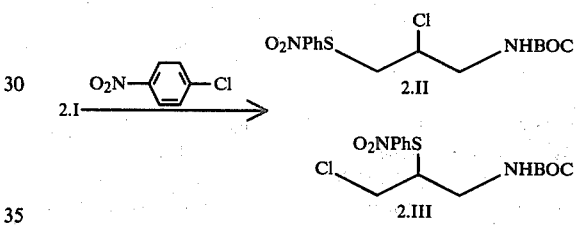

To 781 mg of N-BOC allylamine in 7.5 ml of CH$_2$Cl$_2$ at −18° C. is added dropwise over 2 hours, 1.14 g of p-nitrophenylsulfenyl chloride in 7.5 ml of CH$_2$Cl$_2$. The mixture is stirred 1 hour at 25° C. and evaporated, leaving 2.055 g of crystalline product, which is washed with cyclohexane and recrystallized from 1:1 (v/v) CHCL$_3$-cyclohexane. Pure 2.II, 1.089 g, is obtained crystalline. The combined mother liquors are chromatographed on 60 g of silica gel with 50:1 (v/v) CHCL$_3$-ethylacetate, providing a 1:1 mixture of 2.II and 2.III, 651 mg.

Step C: Preparation of N-BOC 1-amino-2-chloro-3-(p-nitrophenyl)sulfinylpropane (2.IV)

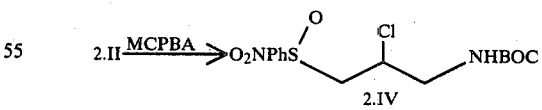

The product from Step B, 2.II, 207 mg, in 9 ml of CH$_2$Cl$_2$ is treated dropwise at 0° C. over 70 minutes with 121 mg of m-chloroperbenzoic acid (MCPBA) (85%) in 9 ml of CH$_2$Cl$_2$ under N$_2$. The solution is stirred 1 hour at 25° C., washed with aqueous NaHCO$_3$, dried with MgSO$_4$, filtered, evaporated (209 mg) and purified by preparative thin layer chromatography on silica gel with 4:1 (v/v) CHCl$_3$-ethylacetate, affording 97 mg of pure product, Rf 0.25.

Step D: Preparation of 1-amino-2-chloro-3-(p-nitrophenyl)sulfinylpropane trifluoroacetate (2.V)

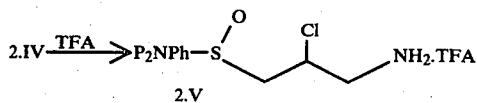

The product from Step C, 78 mg, is dissolved in 0.4 ml of anisole and treated at 0° C. for 10 minutes with 2.0 ml of trifluoroacetic acid (TFA). The TFA and anisole are pumped off at 20° C., and water and $CH_2Cl_2$ are added to the residue. The water layer is separated and evaporated, affording 66 mg of pure product.

EXAMPLE 3

1-p-Nitrophenylsulfinyl-3-aminopropene

Step A: Preparation of 1-p-nitrophenylthio-3-t-butoxycarbonylaminopropene (3.I)

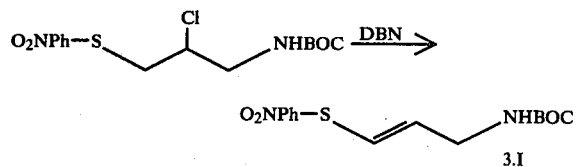

A solution of 346 mg of 1-p-nitrophenylthio-2-chloro-3-BOC-aminopropane (compound 2.I) (1 mmole) and 124 mg (1 mmole) of DBN* in 25 ml benzene is refluxed 3 hours, cooled, filtered and evaporated to provide compound 3.I.
*DBN is 1,5-diazabicyclo[4.3.0]non-5-ene.

Step B: Preparation of 1-p-nitrophenylsulfinyl-3-t-butoxycarbonylaminopropene (3.II)

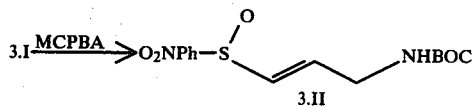

Compound 3.I, 310 mg (1 mmole) is stirred in 20 ml of $CH_2Cl_2$ at 0° C., and to it is added over 1 hour a solution of 203 mg of MCPBA (85% pure; net 172.6 mg, 1 mmole) in 20 ml $CH_2Cl_2$. The reaction mixture is aged 30 minutes at 25°, washed with aqueous $NaHCO_3$ and brine, and evaporated to yield compound 3.II.

Step C: Preparation of 1-p-nitrophenylsulfinyl-3-aminopropane (3.III)

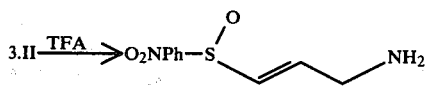

Compound 3.II, 326 mg (1 mmole), is taken up in 1 ml of anisole and at 0° C. treated with 5 ml of TFA for 11 minutes. The TFA and anisole are then pumped off *in vacuo* at 30° C. The product 3.III is isolated as the TFA salt by partitioning between water and $CH_2Cl_2$ and evaporating the aqueous layer to dryness. The free base is obtained if desired from the TFA salt in water by adjusting the pH to 9, extracting into $CH_2Cl_2$ and evaporating the organic solvent.

EXAMPLE 4

Tablets containing 1.0, 2.0, 25.0, 50.0 and 100.0 mg, respectively of 2-amino-4-chloro-5-(p-nitrophenylsulfinyl pentanoic acid (active compound) are prepared as illustrated below:

|  | Amount - mg/tablet | | | | |
| --- | --- | --- | --- | --- | --- |
| Active Compound | 1.0 | 2.0 | 25.0 | 50.0 | 100.0 |
| Microcrystalline cellulose | 49.25 | 48.75 | 37.25 | 100.0 | 200.0 |
| Modified food corn starch | 49.25 | 48.75 | 37.25 | 4.25 | 8.5 |
| Magnesium stearate | 0.50 | 0.50 | 0.50 | 0.75 | 1.5 |

All of the active compound cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 50.0 mg, and 100.0 mg of active compound per tablet.

Other tablets are prepared using the same procedures and the equivalent amounts of excipients along with equivalent amounts of the other active compounds of the present invention.

What is claimed is:

1. A compound of structural formula:

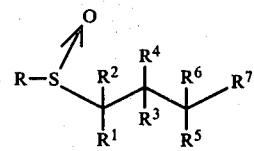

or a pharmaceutically acceptable salt thereof wherein,
R is phenyl, either unsubstituted or substituted with
(1) nitro,
(2) o-$C_{1-3}$ alkyl, or
(3) o,o-di($C_{1-3}$ alkyl),
$R^1$ is hydrogen;
$R^2$ and $R^5$ are hydrogen;
$R^3$ is a facile leaving group selected from
(a) halo
(b) toluenesulfonyloxy,
(c) benzenesulfonyloxy, and
(d) $C_{1-3}$ alkanesulfonyloxy, or
$R^2$ and $R^3$ taken together form a double bond;
$R^4$ is hydrogen;
$R^6$ is hydrogen; and
$R^7$ is —$NH_2$.

2. The compound of claim 1 which is 1-amino-2-chloro-3-p-nitrophenylsulfinyl propane, or 1-p-nitrophenylsulfinyl-3-aminopropene.

* * * * *